US012582779B2

(12) United States Patent
Antonelli et al.

(10) Patent No.: US 12,582,779 B2
(45) Date of Patent: Mar. 24, 2026

(54) MEDICATION DELIVERY DEVICE WITH ROTATION SENSOR

(71) Applicant: Eli Lilly and Company, Indianapolis, IN (US)

(72) Inventors: Matthew Thomas Antonelli, Oakland, CA (US); William Churchill Taliaferro Burke, San Francisco, CA (US); Roy Howard Byerly, Indianapolis, IN (US); Russell Wayne Perkins, Carmel, IN (US); Kenneth Alan Ritsher, Lowell, MA (US); Elias Raad Samia, San Francisco, CA (US); Jayna Jogia, Cambridge (GB); Brian Li-Da Chang, Raleigh, NC (US); Jason Yip Jee Too, Cambridge (GB)

(73) Assignee: Eli Lilly and Company, Indianapolis, IN (US)

( * ) Notice: Subject to any disclaimer, the term of this patent is extended or adjusted under 35 U.S.C. 154(b) by 803 days.

(21) Appl. No.: 17/942,481

(22) Filed: Sep. 12, 2022

(65) Prior Publication Data

US 2023/0001095 A1 Jan. 5, 2023

Related U.S. Application Data

(63) Continuation-in-part of application No. 16/633,630, filed as application No. PCT/US2018/019179 on Feb. 22, 2018, now Pat. No. 11,439,766.

(Continued)

(51) Int. Cl.
*A61M 5/315* (2006.01)

(52) U.S. Cl.
CPC .... *A61M 5/31551* (2013.01); *A61M 5/31585* (2013.01)

(58) Field of Classification Search
CPC .. A61M 5/31568; A61M 5/24; A61M 5/3155; A61M 5/31551; A61M 5/31585
See application file for complete search history.

(56) References Cited

U.S. PATENT DOCUMENTS 7,291,132 B2    11/2007  DeRuntz et al.
9,545,482 B2    1/2017   Binier
          (Continued)

FOREIGN PATENT DOCUMENTS

CN    102413759 A    4/2012
CN    104203315 A    12/2014
          (Continued)

OTHER PUBLICATIONS

Patent Cooperation Treaty International Search Report pertaining to International Application No. PCT/US2018/019179; International Filing Date: Feb. 22, 2018; Date of Mailing: May 15, 2018.
(Continued)

*Primary Examiner* — Dung T Ulsh
(74) *Attorney, Agent, or Firm* — M. Daniel Spillman

(57) ABSTRACT

The present disclosure relates to a dose detection system for use with a medication delivery device in which a dose setting member rotates relative to an actuator during dose delivery. The dose detection system comprises a module including a rotation sensor attached to the actuator during dose delivery. A sensed element is attached to the dose setting member and includes first gear teeth. The rotation sensor comprises a driven gear including second gear teeth. The second gear teeth are operatively received by the first gear teeth and are driven in rotation as the first gear teeth rotate during dose delivery. The rotation sensor is responsive to the rotation of the second gear teeth to detect the rotation of the dose setting member.

20 Claims, 6 Drawing Sheets

Related U.S. Application Data

(60) Provisional application No. 62/548,059, filed on Aug. 21, 2017.

(56) References Cited

U.S. PATENT DOCUMENTS

| | | | |
|---|---|---|---|
| 2008/0033369 A1* | 2/2008 | Kohlbrenner | A61M 5/20 604/207 |
| 2014/0194829 A1 | 7/2014 | Baek et al. | |
| 2016/0030680 A1* | 2/2016 | Veasey | A61M 5/3155 604/211 |
| 2016/0082192 A1 | 3/2016 | Veasey et al. | |

FOREIGN PATENT DOCUMENTS

| | | |
|---|---|---|
| EP | 2692378 | 2/2014 |
| EP | 3103492 | 12/2016 |
| EP | 3184137 | 6/2017 |
| WO | 20020064196 | 8/2002 |
| WO | 2010098927 | 9/2010 |
| WO | 2014111342 | 7/2014 |
| WO | 2014111343 | 7/2014 |
| WO | 2016113348 | 7/2016 |
| WO | 2017097507 | 6/2017 |
| WO | 2018013419 | 1/2018 |
| WO | 2018160425 | 9/2018 |

OTHER PUBLICATIONS

Patent Cooperation Treaty Written Opinion of the International Searching Authority pertaining to International Application No. PCT/US2018/019179; International Filing Date: Feb. 22, 2018; Date of Mailing: May 15, 2018.

* cited by examiner

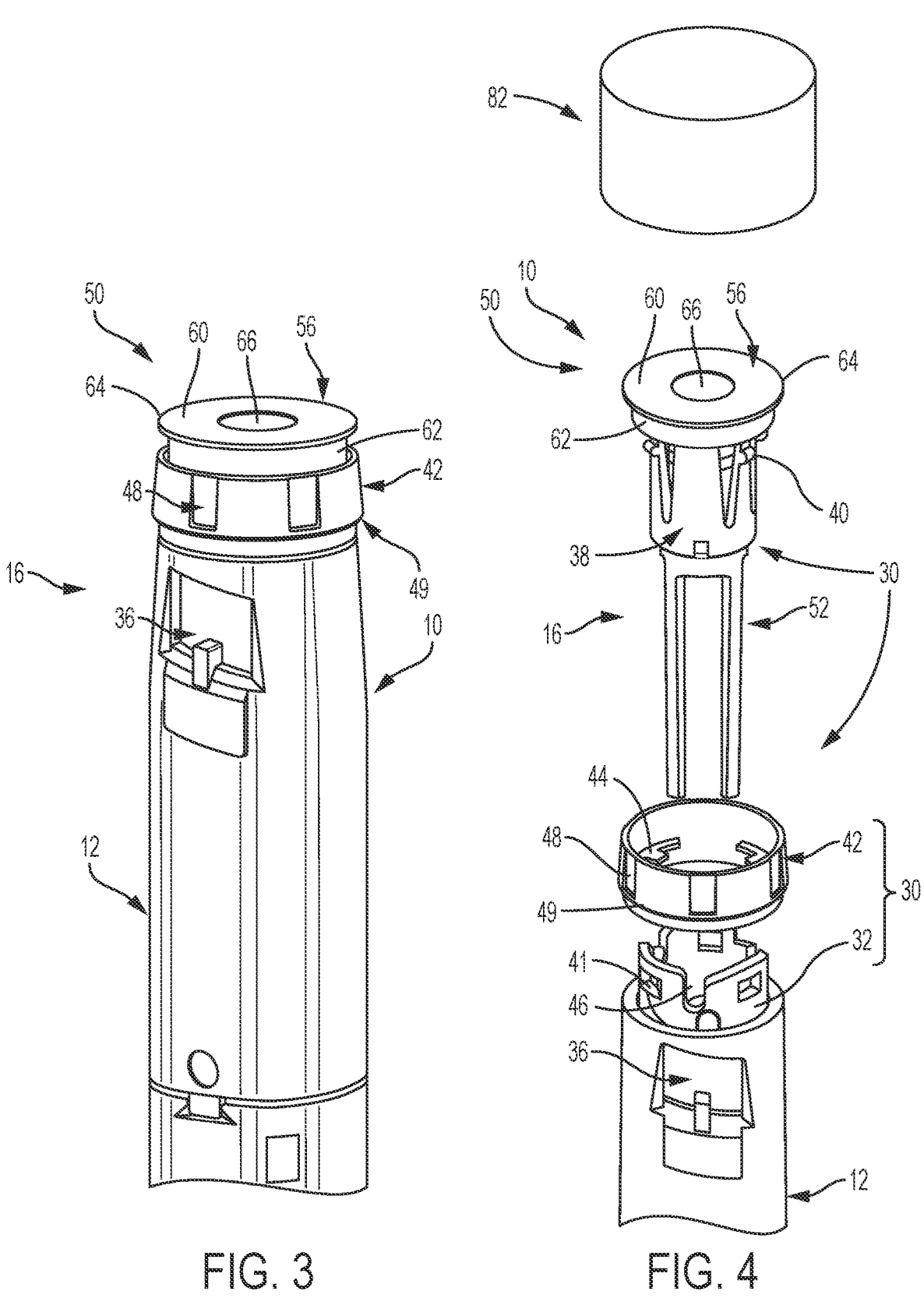
FIG. 3                                    FIG. 4

MEDICATION DELIVERY DEVICE WITH ROTATION SENSOR

TECHNICAL FIELD

The present disclosure relates to an electronic dose detection system for a medication delivery device, and illustratively to an electronic dose detection module adapted to removably attach to a proximal end portion of a medication delivery device. The dose detection system is operable to detect the amount of a dose of medication delivered by the medication delivery device.

BACKGROUND

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device, and which detects the relative movement of a sensed component secured to a second member of the device.

The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by the medication delivery device during an injection event. Further, there is a need for such a dose detection device to be removable and reusable with multiple delivery devices.

SUMMARY

In accordance with an aspect of the present disclosure, a dose detection system is provided for a medication delivery device which includes a dose setting member which rotates relative to an actuator during dose delivery. The dose detection system comprises an electronics assembly attached to the actuator and a sensed element attached to the dose setting member. The electronics assembly includes a rotation sensor operable with the sensed element to detect the movement of the dose setting member relative to the actuator during dose delivery. The electronics assembly may further include various additional components such as one or more other sensors, memory, a processor, a controller, a battery, etc.

In another aspect, the dose detection system comprises a module which is removably attachable to the medication delivery device. Among other advantages, the attachable and detachable module is operative to detect a delivered medication amount without changing the functionality or operation of the medication delivery device to which it is attached. In some embodiments, the sensing system records the size of the delivered dose and communicates the information to an external device. The medication delivery device may include a medication. Other advantages will be recognized by those of ordinary skill in the art.

BRIEF DESCRIPTION OF THE DRAWINGS

The features and advantages of the present disclosure will become more apparent to those skilled in the art upon consideration of the following detailed description taken in conjunction with the accompanying figures.

FIG. 3 is a perspective view of the proximal portion of the exemplary medication delivery device of FIG. 1.

FIG. 4 is a partially-exploded, perspective view of the proximal portion of the exemplary medication delivery device of FIG. 1, and showing a dose detection module.

DETAILED DESCRIPTION

Figure 1:
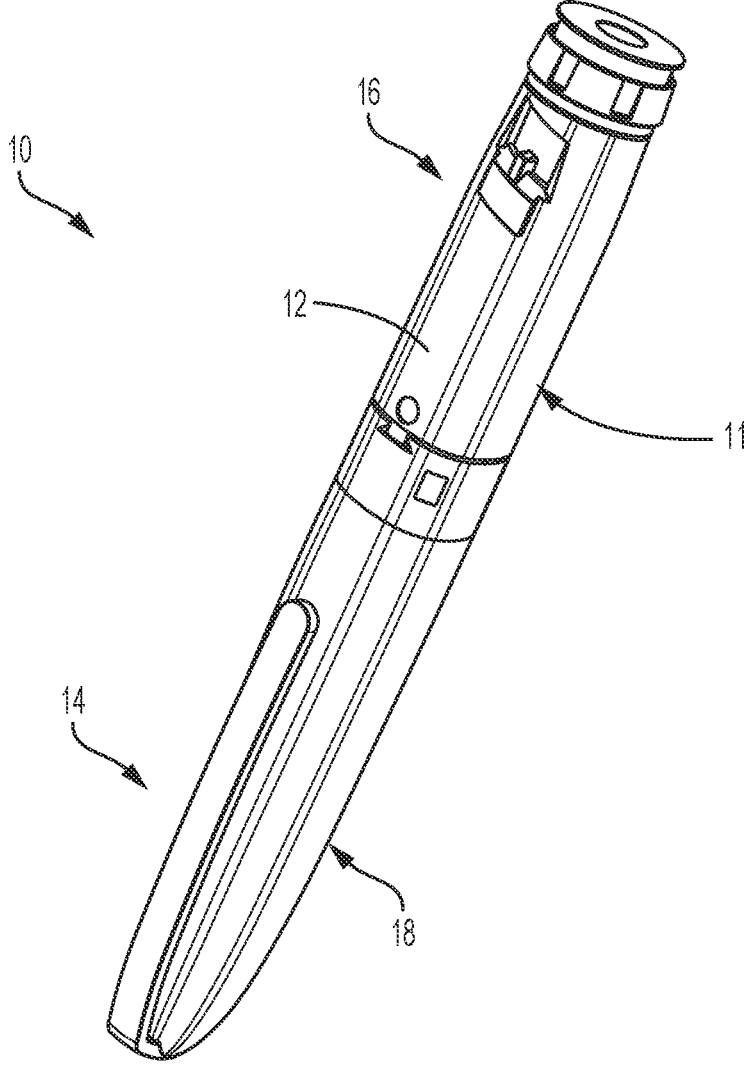
FIG. 1 is a perspective view of an exemplary medication delivery device with which the dose detection system of the present disclosure is operable.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for determining the amount of a dose delivered by a medication delivery device based on the sensing of relative rotational movement between a dose setting member and an actuator of the medication delivery device. The sensed relative rotational movements are correlated to the amount of the dose delivered. By way of illustration, the medication delivery device is described in the form of a pen injector. However, the medication delivery device may be any device which is used to set and to deliver a dose of a medication, such as a pen injector, an infusion pump or a syringe. The medication may be any of a type that may be delivered by such a medication delivery device.

Devices described herein, such as device 10, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dula-glutide or liraglutide, glucagon, glucagon analogs, glucagon derivatives, gastric inhibitory polypeptide (GIP), GIP ana-logs, GIP derivatives, oxyntomodulin analogs, oxyntomodu-lin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
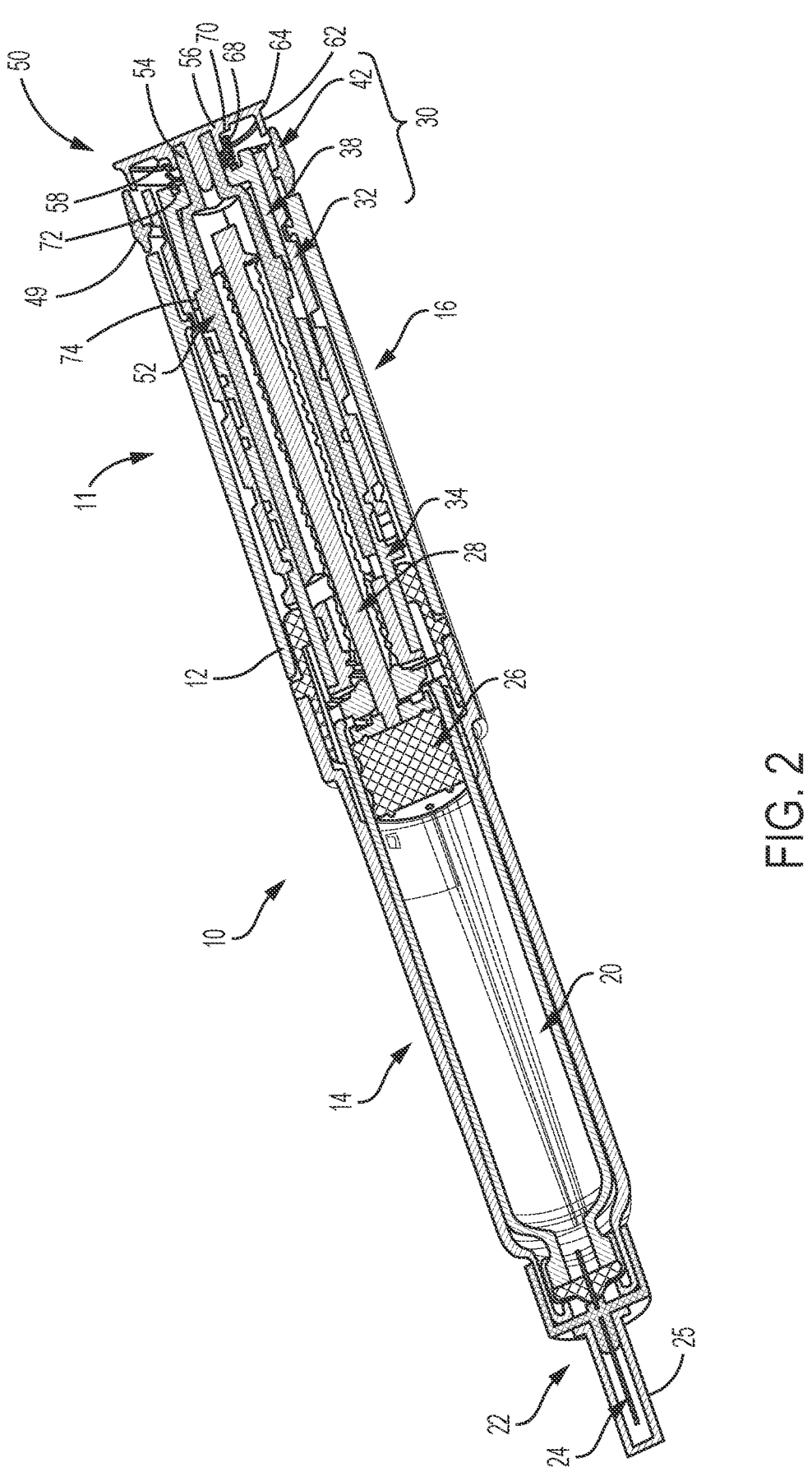
FIG. 2 is a cross-sectional perspective view of the exemplary medication delivery device of FIG. 1.

An exemplary medication delivery device 10 is illustrated in FIGS. 1-4 as a pen injector configured to inject a medication into a patient through a needle. Pen injector 10 includes a body 11 comprising an elongated, pen-shaped housing 12 including a distal portion 14 and a proximal portion 16. Distal portion 14 is received within a pen cap 18. Referring to FIG. 2, distal portion 14 contains a reservoir or cartridge 20 configured to hold the medicinal fluid to be dispensed through its distal outlet end during a dispensing operation. The outlet end of distal portion 14 is equipped with a removable needle assembly 22 including an injection needle 24 enclosed by a removable cover 25.

A piston 26 is positioned in reservoir 20. An injecting mechanism positioned in proximal portion 16 is operative to advance piston 26 toward the outlet of reservoir 20 during the dose dispensing operation to force the contained medi-cine through the needled end. The injecting mechanism includes a drive member 28, illustratively in the form of a screw, axially moveable relative to housing 12 to advance piston 26 through reservoir 20.

A dose setting member 30 is coupled to housing 12 for setting a dose amount to be dispensed by device 10. In the illustrated embodiment, dose setting member 30 is in the form of a screw element operative to spiral (i.e., simultane-ously move axially and rotationally) relative to housing 12 during dose setting and dose dispensing. FIGS. 1 and 2 illustrate the dose setting member 30 fully screwed into housing 12 at its home or zero dose position. Dose setting member 30 is operative to screw out in a proximal direction from housing 12 until it reaches a fully extended position corresponding to a maximum dose deliverable by device 10 in a single injection.

Referring to FIGS. 2-4, dose setting member 30 includes a cylindrical dose dial member 32 having a helically threaded outer surface that engages a corresponding threaded inner surface of housing 12 to allow dose setting member 30 to spiral relative to housing 12. Dose dial member 32 further includes a helically threaded inner sur-face that engages a threaded outer surface of sleeve 34 (FIG. 2) of device 10. The outer surface of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotation-ally locked to dose dial member 32 by detents 40 received within openings 41 in dial member 32. Dose setting member 30 further includes a skirt or collar 42 positioned around the outer periphery of dial member 32 at its proximal end. Skirt 42 is axially and rotationally locked to dial member 32 by tabs 44 received in slots 46 formed by dose dial member 32.

Dose setting member 30 therefore may be considered to comprise any or all of dose dial member 32, flange 38, and skirt 42, as they are all rotationally and axially fixed together. Dose dial member 32 is directly involved in setting the dose and driving delivery of the medication. Flange 38 is attached to dose dial member 32 and, as described later, cooperates with a clutch to selectively couple dose dial member 32 with a dose button.

Skirt 42 provides a surface external of body 11 to enable a user to rotate dose dial member 32 for setting a dose. Skirt 42 illustratively includes a plurality of surface features 48 and an annular ridge 49 formed on the outer surface of skirt 42. Surface features 48 are illustratively longitudinally extending ribs and grooves that are circumferentially spaced around the outer surface of skirt 42 and facilitate a user's grasping and rotating the skirt. In an alternative embodi-ment, skirt 42 is removed or is integral with dial member 32, and a user may grasp and rotate dose dial member 32 for dose setting.

Delivery device 10 includes an actuator 50 having a clutch 52 which is received within dose dial member 32. Clutch 52 includes an axially extending stem 54 at its proximal end. Actuator 50 further includes dose button 56 positioned proximally of skirt 42 of dose setting member 30. Dose button 56 includes a mounting collar 58 (FIG. 2) centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inward of the outer peripheral edge of face 60 to form an annular lip 64 there between. Face 60 of dose button 56 serves as a push surface against which a force can be applied manually, i.e., directly by the user to push actuator 50 in a distal direction. Dose button 56 illustratively includes a recessed portion 66 centrally located on proximal face 60, although proximal face 60 alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation.

Delivery device 10 is operable in both a dose setting mode and a dose dispensing mode. In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one incre-ment or "click" may equal one-half or one unit of medica-tion. The set dose amount is visible to the user via the dial indicator markings shown through dosage window 36. Actuator 50, including dose button 56 and clutch 52, move axially and rotationally with dose setting member 30 during the dialing in the dose setting mode.

Dose dial member 32, flange 38 and skirt 42 are all fixed rotationally to one another, and rotate and extend proximally of the medication delivery device 10 during dose setting, due to the threaded connection of dose dial member 32 with housing 12. During this dose setting motion, dose button 56 is rotationally fixed relative to skirt 42 by complementary splines 74 of flange 38 and clutch 52 (FIG. 2), which are urged together by bias member 68. In the course of dose setting, skirt 42 and dose button 56 move relative to housing 12 in a spiral manner from a "start" position to an "end" position. This rotation relative to the housing is in proportion to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56. The axial force is applied by the user directly to dose button 56. This causes axial movement of actuator 50 in the distal direction relative to housing 12.

The axial shifting motion of actuator 50 compresses biasing member 68 and reduces or closes the gap between dose button 56 and tubular flange 38. This relative axial movement separates the complementary splines 74 on clutch 52 and flange 38, and thereby disengages actuator 50, e.g., dose button 56, from being rotationally fixed to dose setting member 30. In particular, dose setting member 30 is rotationally uncoupled from actuator 50 to allow backdriving rotation of dose setting member 30 relative to actuator 50 and housing 12. Also, since dose setting member 30 and actuator 50 are free to relatively rotate, actuator 50 is held from rotating relative to device housing 12 by the user's engagement of dose button 56 by pressing against it.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3.

The dose delivered may be derived based on the rotation of dose setting member 30 relative to actuator 50 during dose delivery. This rotation may be determined by detecting the incremental movements of the dose setting member which are "counted" as the dose setting member is rotated during dose delivery.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein.

The dose detection systems use a sensing component and a sensed component attached to members of the medication delivery device. The term "attached" encompasses any manner of securing the position of a component to another component or to a member of the medication delivery device such that they are operable as described herein. For example, a sensing component may be attached to a member of the medication delivery device by being directly positioned on, received within, integral with, or otherwise connected to, the member. Connections may include, for example, connections formed by frictional engagement, splines, a snap or press fit, sonic welding or adhesive.

The term "directly attached" is used to describe an attachment in which two components, or a component and a member, are physically secured together with no intermediate member, other than attachment components. An attachment component may comprise a fastener, adapter or other part of a fastening system, such as a compressible membrane interposed between the two components to facilitate the attachment. A "direct attachment" is distinguished from an attachment where the components/members are coupled by one or more intermediate functional members, such as the way dose dial member 32 is coupled in FIG. 2 to dose button 56 by clutch 52.

The term "fixed" is used to denote that an indicated movement either can or cannot occur. For example, a first member is "fixed rotationally" with a second member if the two members are required to move together in rotation. In one aspect, a member may be "fixed" relative to another member functionally, rather than structurally. For example, a member may be pressed against another member such that the frictional engagement between the two members fixes them together rotationally, while the two members may not be fixed together absent the pressing of the first member.

Various sensor systems are contemplated herein. In general, the sensor systems comprise a sensing component and a sensed component. The term "sensing component" refers to any component which is able to detect the relative position or movement of the sensed component. The sensing component includes a sensing element, or "sensor", along with associated electrical components to operate the sensing element. The "sensed component" is any component for which the sensing component is able to detect the position and/or movement of the sensed component relative to the sensing component. For the dose detection system, the sensed component rotates relative to the sensing component, which is able to detect the rotational movement of the sensed component. The sensing component may comprise one or more sensing elements, and the sensed component may comprise one or more sensed elements.

The sensor system produces outputs representative of the movement of the sensed component. A controller is operably connected to the sensor to receive the outputs. The controller is configured to determine from the outputs the amount of dose delivered by operation of the medication delivery device.

Illustratively, the dose detection system includes an electronics assembly suitable for operation of the sensor system as described herein. A controller is operably connected to the sensor system to receive outputs from the rotation sensor. The controller is configured to determine from the outputs the amount of dose delivered by operation of the medication delivery device. The controller may include conventional components such as a processor, power supply, memory, microcontrollers, etc. Alternatively, at least some components may be provided separately, such as by means of a computer, smart phone or other device. Means are then provided to operably connect the external controller components with the sensor system at appropriate times, such as by a wired or wireless connection.

An exemplary electronics assembly 76 comprises a flexible printed circuit board (FPCB) having a plurality of electronic components. The electronics assembly comprises a sensor system including one or more sensors operatively communicating with a processor for receiving signals from the sensor representative of the sensed rotation. Electronics assembly 76 further includes a microcontroller unit (MCU) comprising at least one processing core and internal memory. The system includes a battery, illustratively a coin cell battery, for powering the components. The MCU includes control logic operative to perform the operations described herein, including determining a dose delivered by medication delivery device 10 based on a detected rotation of the dose setting member relative to the actuator. Many of the components of the electronics assembly may be contained in a compartment 78 located proximal of the dose button 56.

The MCU is operative to store the detected dose delivery in local memory (e.g., internal flash memory or on-board EEPROM). The MCU is further operative to wirelessly transmit a signal representative of the detected dose to a paired remote electronic device, such as a user's smartphone. Transmission may, for example, be over a Bluetooth low energy (BLE) or other suitable short or long range wireless communication protocol. Illustratively, the BLE control logic and MCU are integrated on the same circuit.

Further disclosed herein is a medication delivery device including a dose detection system operable to determine the amount of dose delivered based on relative rotation between a dose setting member and the device body. The dose detection system utilizes a dose setting member attached to the device body and rotatable relative to the device body about an axis of rotation during dose delivery. A sensed element is attached to and rotationally fixed with the dose setting member. An actuator is attached to the device body and is held against rotation relative to the device body during dose delivery. The sensed element thereby rotates relative to the actuator during dose delivery in relation to the amount of dose delivered.

The dose detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable. The sensor system is operable to determine the total angular displacement of a dose setting member during dose delivery. Thus, if the angular displacement is 90°, then 5 units of dose have been delivered.

The angular displacement is determined by counting increments of dose amounts as the injection proceeds. For example, a sensing system may use a repeating pattern of a sensed element, such that each repetition is an indication of a predetermined degree of angular rotation. Conveniently, the pattern may be established such that each repetition corresponds to the minimum increment of dose that can be set with the medication delivery device.

The sensor system components may be permanently or removably attached to the medication delivery device. In an illustrative embodiment, as least some of the dose detection system components are provided in the form of a module that is removably attached to the medication delivery device. This has the advantage of making these sensor components available for use on more than one pen injector.

The sensor system detects during dose delivery the relative rotation of the sensed component, and therefore of the dose setting member, from which is determined the amount of a dose delivered by the medication delivery device. In an illustrative embodiment, a rotation sensor is attached, and rotationally fixed, to the actuator. The actuator does not rotate relative to the body of the medication delivery device during dose delivery. In this embodiment, a sensed component is attached, and rotationally fixed, to the dose setting member, which rotates relative to the actuator and the device body during dose delivery.

The sensor system includes a rotation sensor attached to the actuator. The sensed element includes a cylindrical drive surface centered on a first axis of rotation corresponding to the axis of rotation of the dose setting member. The rotation sensor includes a driven member including a driven surface received by the drive member to move the driven member in response to rotation of the sensed element. Illustratively, the driven member is a circular component, such as a gear, which rotates in response to rotation of the drive member, which may for example comprise a drive gear. The rotation sensor is responsive to the movement of the driven member and generates signals corresponding to the amount of a dose delivery. A controller is responsive to the signals generated by the rotation sensor to determine the amount of dose delivery based on the detected rotation of the dose setting member relative to the actuator during dose delivery.

The drive and driven members may comprise anything which provides for transfer of the rotation of the sensed element to a detectable second movement. In a broad sense, the movement of the driven member may be in any manner, such as linear or rotational. Illustratively, the driven member rotates about a second axis of rotation, which may be the same as or different than the first axis of rotation of the dose setting member. In a particular aspect, the driven member rotates about a second axis of rotation that is identical with or parallel to the first axis of rotation.

The drive surface of the sensed element includes surface features which couple with the driven surface of the driven member. By way of example, the coupling between the drive surface and the driven surface may be a frictional engagement between the two. In one aspect, the drive and driven members are gears comprising sets of intermeshed teeth.

Figure 5:
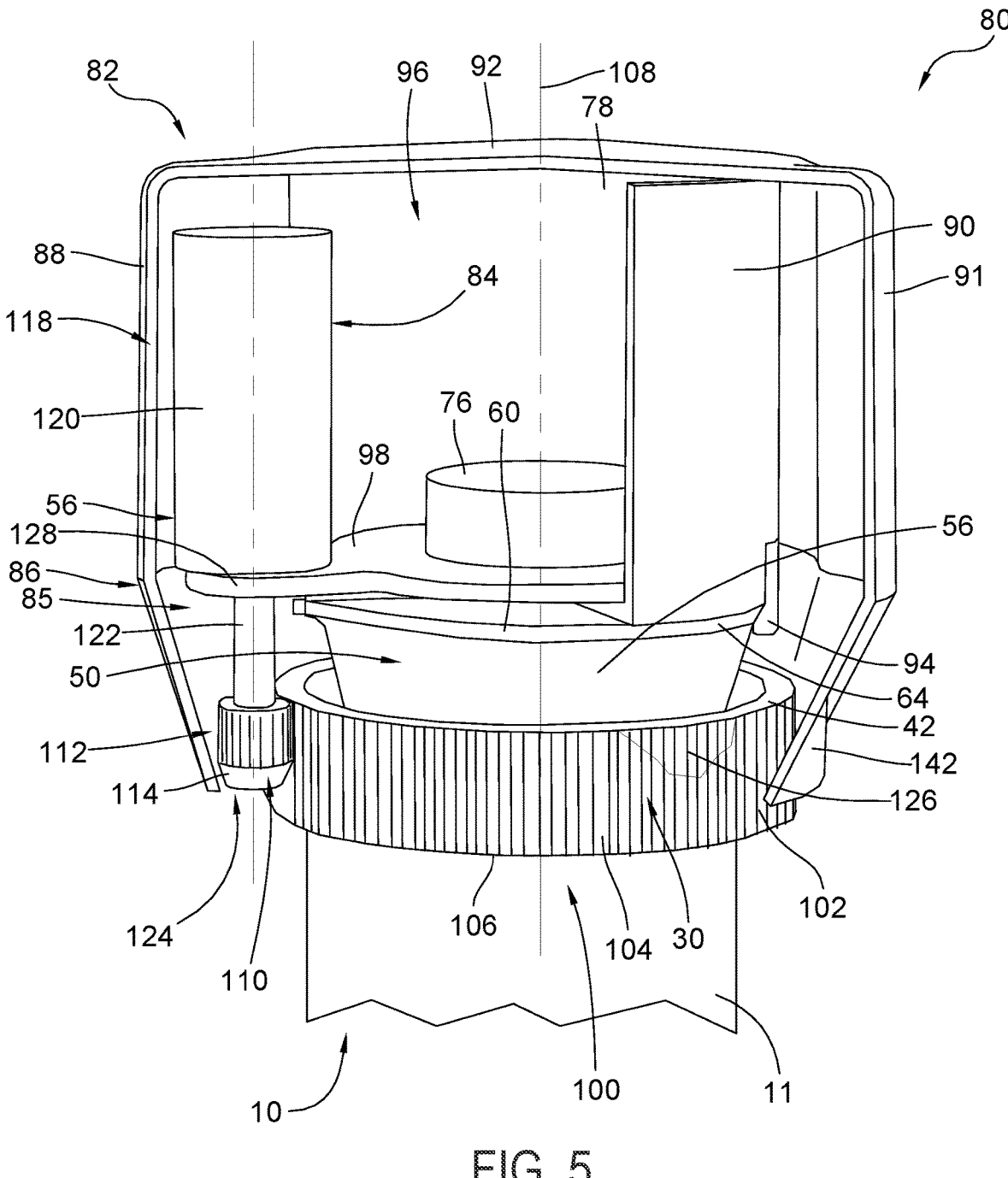
FIG. 5 is a perspective, diagrammatic view, partially in cross section, of an exemplary embodiment of a dose detection system shown attached to the proximal portion of a medication delivery device.

Referring to FIG. 5, there is shown in diagrammatic form a dose detection system 80 including a module 82 useful in combination with a medication delivery device, such as device 10. Module 82 carries a sensor system, shown generally at 84, including a sensing component 85 comprising a rotation sensor 86 and other associated components such as a processor, memory, battery, etc. Module 82 may be provided as a separate component which may be removably attached to the actuator.

Dose detection module 82 includes a body 88 attached to dose button 56. Body 88 illustratively includes an inner wall 90, an outer wall 91, and a top wall 92, spanning over and sealing inner wall 90. By way of example, in FIG. 5 inner wall 90 is diagrammatically shown having inwardly-extending tabs 94 attaching module 82 to dose button 56. Module 82 is thereby attached to dose button 56 such that pressing on the module delivers a set dose.

Dose detection module 82 may alternatively be attached to dose button 56 via any suitable fastening means, such as a snap or press fit, threaded interface, etc., provided that in one aspect module 82 may be removed from a first medication delivery device and thereafter attached to a second medication delivery device. The attachment may be at any location on dose button 56, provided that dose button 56 is able to move any required amount axially relative to dose setting member 30, as discussed herein.

During dose delivery, dose setting member 30 is free to rotate relative to dose button 56 and module 82. In an illustrative embodiment, module 82 is rotationally fixed with dose button 56 and does not rotate during dose delivery. This may be provided structurally, such as with tabs 94 of FIG. 5, or by having mutually-facing splines or other surface features on the module body 88 and dose button 56 engage upon axial movement of module 82 relative to dose button 56. In another embodiment, the distal pressing of the module provides a sufficient frictional engagement between module 82 and dose button 56 as to functionally cause the module 82 and dose button 56 to remain rotationally fixed together during dose delivery.

Top wall 92 is spaced apart from face 60 of dose button 56 and thereby provides with inner wall 90 a compartment 78 containing some or all of electronics assembly 76. Compartment 78 defines a chamber 96 and may be open at the bottom, or may be enclosed, such as by a bottom wall 98. Bottom wall 98 may be positioned to bear directly against face 60 of dose button 56. Alternatively, bottom wall 98, if present, may be spaced apart from dose button 56, and other contacts between module 82 and dose button 56 may be used such that an axial force applied to module 82 is transferred to dose button 56.

Referring to FIG. 5, there is diagrammatically shown a dose detection system 80 further comprising a sensed element 100 attached to dose setting member 30. As previously described, dose setting member 30 may comprise several separate components which are axially and rotationally fixed together. Accordingly, sensed element 100 may be attached to any component of dose setting member 30 which rotates relative to actuator 50 during dose delivery in proportion to the amount of the dose delivery. In the embodiment shown in FIG. 5, sensed element 100 is attached to skirt 42.

Sensed element 100 includes a cylindrical outer surface 102 comprising a drive surface 104. Illustratively, drive surface 104 may include first gear teeth 106. Dose setting member 30, and particularly in this case skirt 42, is rotatable relative to actuator 60 about a first axis of rotation 108. First gear teeth 106 are radially-spaced about the first axis of rotation 108.

Actuator 60, which includes dose button 56, is mounted to delivery device 10 to operate in two modes. In a first operating mode, during dose setting, actuator 60 is axially and rotationally fixed with dose setting member 30. In a second operating mode during dose delivery, actuator 60 is held against rotation relative to device body 11 and sensed element 100 and dose setting member 30 rotate relative to actuator 60 in relation to the amount of dose delivered.

Rotation sensor 86 is attached to actuator 60 during dose delivery. Rotation sensor 86 includes a contact component 110 including a driven surface 112 which operatively engages with drive surface 104. As previously noted, the operative engagement between drive surface 104 and driven surface 112 may be provided in any manner which transfers the rotation of sensed element 100 to contact component 110. This may comprise, for example, a frictional engagement between the drive and driven surfaces. In the embodiment of FIG. 5, drive surface 104 is shown as having first gear teeth 106 which in this case extend radially outward. A corresponding set of second gear teeth 114 are then preferably provided on the driven surface 112. The second gear teeth 114 are illustratively provided as being radially-spaced about a second axis of rotation 116, which in FIG. 5 is shown as being separate from the first axis of rotation.

Contact component 110 is used by rotation sensor 86 to detect the amount of rotation of dose setting member 30 during dose delivery, and may be provided in various ways. Generally, rotation sensor 86 includes a number of components which operate together to convert a detected rotation of contact component 110 into an amount of rotation of sensed element 100, and therefore of dose setting member 30. As shown in FIG. 5, for example, rotation sensor 86 may comprise an encoder 118. An example of an encoder useful in this manner is a micro encoder such as Miniature Opto-electronic Encoder Series MOT7 and available from Megatron. Such encoders are well known in the art.

In another example, rotation sensor 86 may comprise a multi-turn potentiometer that uses variable resistance to determine data indicative of the amount of rotation of the dose setting member. Although the following description focuses on the components, arrangement, and orientation of the encoder 118, the components, arrangement, and orientation may also be referenced for the multi-turn potentiometer, which includes a body, a shaft, a contact component, a drive gear comprising the second gear teeth. For example, the multi-turn potentiometer may be oriented with its body positioned proximal of the dose setting member 30. The shaft of the multi-turn potentiometer may extend distally below from its body to position the contact component of the of the multi-turn potentiometer and the associated driven surface axially aligned with the dose setting member 30. The sensed element may be provided as a cylindrical member attached to or formed integrally with the dose setting member 30. The drive gear of the multi-turn potentiometer may be thereby positioned with its second gear teeth axially aligned with first gear teeth 106. The multi-turn potentiometer may comprise, or be electrically connected to, a voltmeter or resistance sensor configured to measure an electrical resistance between two electrical leads that extend from the potentiometer. As rotation of the sensed element drives rotation of contact component 110 as previously described, the electrical resistance measured between said electrical leads may increase or decrease. For instance, as the contact component 110 rotates in a first direction, the electrical resistance may increase. Conversely, as the contact component 110 rotates in a second direction opposite to the first direction, the electrical resistance may decrease. By measuring the electrical resistance across the multi-turn potentiometer, a controller (which may be part of electronics assembly 76) may determine an absolute rotational position of the multi-turn potentiometer. Alternatively, or additionally, by measuring a change in electrical resistance measured across the multi-turn potentiometer, the controller may determine an amount of rotation of contact component 110, and therefore an amount of rotation of sensed element 100 and dose setting member 30. Such multi-turn potentiometers are well known in the art.

Referring again to FIG. 5, encoder 118 includes a body 120, shaft 122, and contact component 110. In the exemplified embodiment, contact component 110 comprises a drive gear 124 comprising second gear teeth 114 meshed with the first gear teeth 106 of sensed element 100. Second gear teeth 114 are thereby operatively received by first gear teeth 106 such that second gear teeth 114 are driven in rotation about second axis of rotation 116 as first gear teeth rotate about first axis of rotation 108 during rotation of sensed element 100 relative to actuator 60 during dose delivery.

As shown in FIG. 5, illustratively encoder 118 is oriented with body 120 positioned proximal of actuator 50, and particularly proximal of dose button 56. Shaft 122 extends distally below face 60 of dose button 56 to position contact component 110 and associated driven surface 112 axially aligned with dose setting member 30. In this embodiment, sensed element 100 is provided as a cylindrical member attached to the exposed external surface 126 of skirt 42. The drive gear 124 is thereby positioned with second gear teeth 114 axially aligned with first gear teeth 106.

Module 82 includes a bottom wall 98 from which tabs 94 extend for coupling with annular lip 64 of dose button 56. Module 82 is thus attached to dose button 56 by distally moving the module against the dose button until a snap fit occurs. Module 82 is thereby removably attached to actuator 50, and in this case specifically to dose button 56. As mentioned previously, however, alternative forms of attachment may also be used.

Bottom wall 98 of module 82 includes a projection 128 from bottom wall 98 attaching encoder 118 to module 82. This positions the attachment of rotation sensor 86 close to electronics assembly 76 to facilitate connection therebetween. However, alternately, rotation sensor 86 may be attached to inner wall 90, outer wall 91, or other components of module 82. Encoder 118 is operably connected with electronics assembly 76 contained by module 82.

The components of encoder 118 are operable to be responsive to the rotation of the second gear teeth 116 to detect rotation of dose setting member 30. A controller (not shown) is provided as a component of the electronics assembly 76. The controller is operable to receive signals from rotation sensor 86 which are indicative of rotation of sensed element 100 during dose delivery, and to determine therefrom the amount of the dose delivered.

Module 82 thus includes rotation sensor 86 in a manner removably attached to device 10, and provides a method for using the rotation sensor with a number of such devices. Sensed element 100 may also be a separate, add-on component to complement the use of module 82. For example, sensed element 100 may be a separate member removably attached to skirt 42 or another component of dose setting member 30. Such attachment of sensed element 100 may be in any operable manner, such as by a snap fit (as shown), frictional fit, interlocking of mutually-facing splines, etc. Contact component 110 may be provided with a tapered lower end to facilitate meshing of first gear teeth with second gear teeth 14 during mounting of module 82 to dose button 56.

In one embodiment, dose setting member 30 comprises an exterior surface 1268 exposed outside of body 11 of medication delivery device 10. Exposed exterior surface 126 is useful, in the absence of dose detection system 80, for the user to rotate dose setting member 30 to set a dose. In use with module 82, sensed element 100 is attached to exposed exterior surface 126 in any manner suitable for rotationally fixing sensed element 100 to dose setting member 30, while also being removable therefrom.

Figure 6:
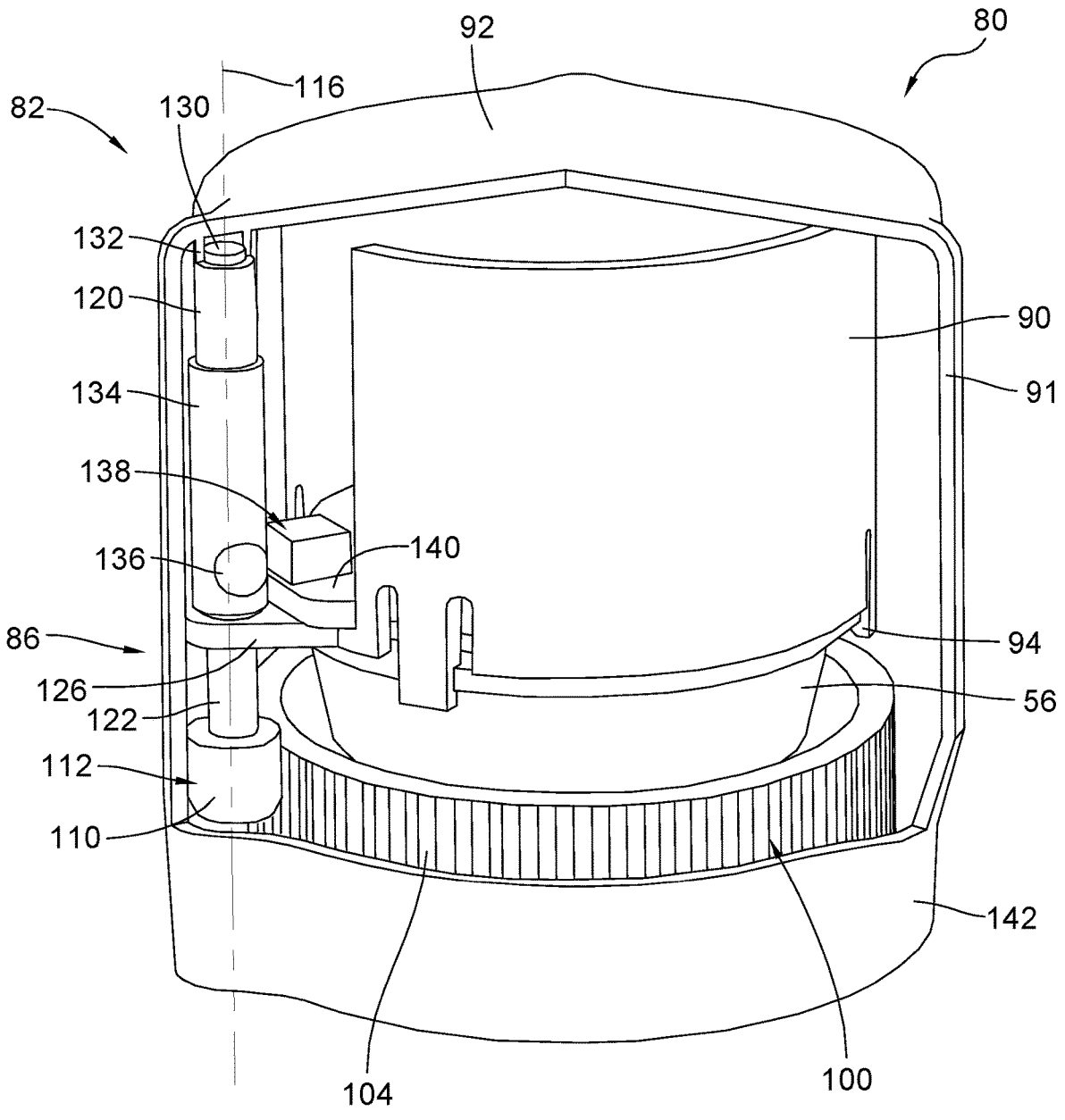
FIG. 6 is a perspective, diagrammatic view, partially in cross section, of a second exemplary embodiment of a dose detection system shown attached to the proximal portion of a medication delivery device.

Referring to FIG. 6, there is shown an alternative to the embodiment of FIG. 5 in which a particular type of rotation sensor is used to detect rotation of sensed element 100. Rotation sensor 86 is attached to projection 128 and includes body 120 rotationally attached at its proximal end 130 to coupling 132 extending distally from top wall 92. Rotation sensor 86 further includes an outer sleeve 134 carrying a magnet 136. A Hall or other magnetic sensor 138, is attached to printed circuit board 140. With rotation of sensed element 100 during dose delivery, drive surface 104 moves driven surface 112 in rotation about second axis 116. Shaft 122, body 120 and sleeve 134 move in rotation with driven surface 112. Magnet 136 is caused to rotate through the area sensed by magnetic sensor 138, which generates signals representative of the rotation of sensed element 100, and therefore of dose setting member 30. It will be appreciated that various other sensing systems may be used to detect the rotation of contact component 110.

For the embodiments of FIGS. 5 and 6, sensed element 100 is positioned distally of the proximal surface 60 of dose button 56. While not required, sensed element 100 is positioned in axial alignment with the exposed exterior surface 126 of skirt 42. Second gear teeth 114 are axially-aligned with the first gear teeth 106 and with exposed exterior surface 126. Outer wall 91 includes a lower portion 142 (FIG. 6) which extends distally beyond dose button 56 to axially cover the first and second gear teeth. In this manner, module 82 prevents the user from making inadvertent contact with sensed element 100 or contact component 110.

Figure 7:
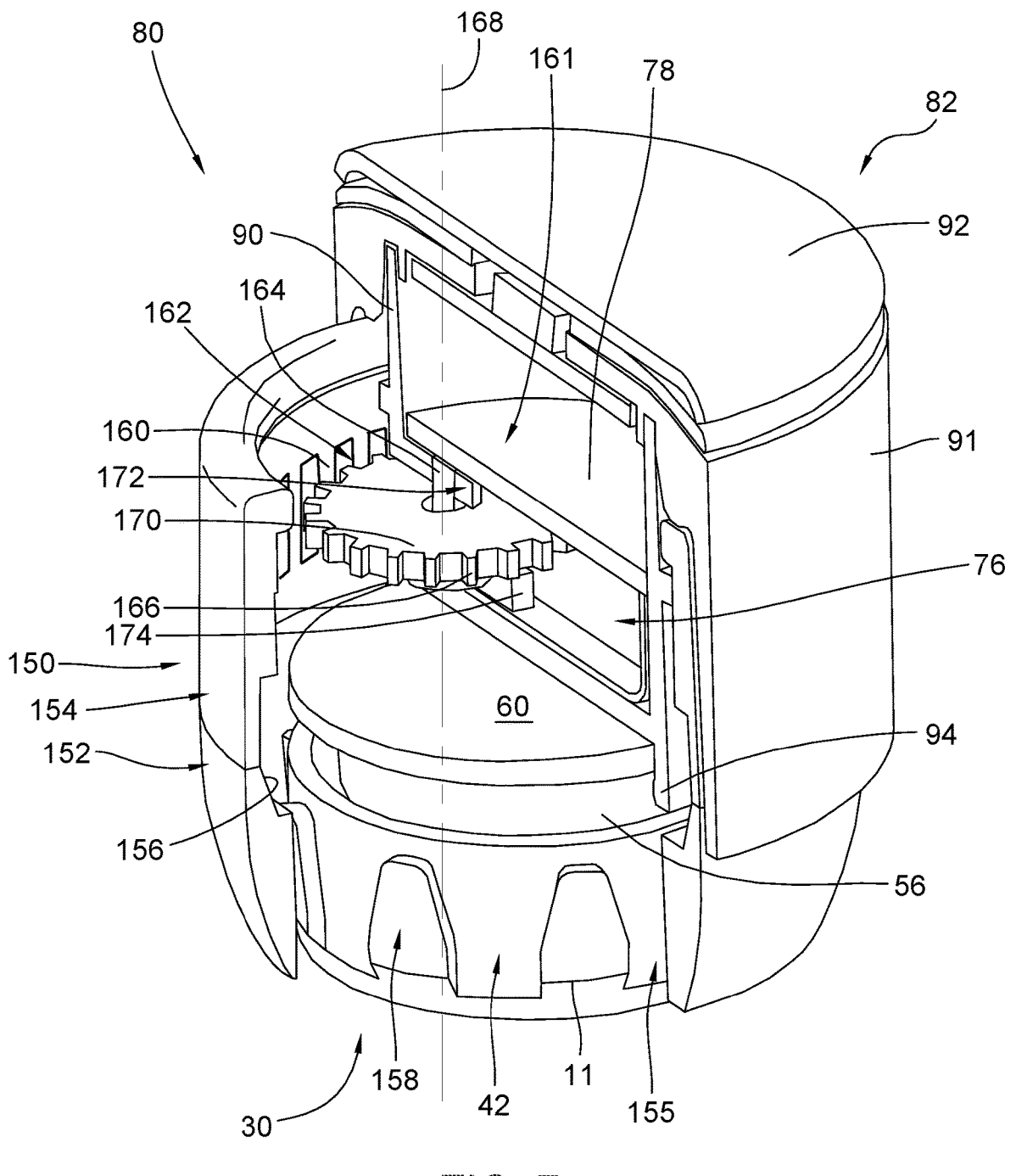
FIG. 7 is a perspective, diagrammatic view, partially in cross section, of a third exemplary embodiment of a dose detection system shown attached to the proximal portion of a medication delivery device.

In FIG. 7 there is shown another exemplary embodiment of the dose detection system. As before, system 80 includes a module 82 including an inner wall 90 secured by tabs 94 to dose button 56. Module 82 further includes outer wall 91 and top wall 92. Inner wall 90 and top wall 92 together define a compartment 78 containing an electronics assembly.

A sensed element 150 comprises a coupling member 152 attached to an extending member 154. Coupling member 152 is attached to exposed exterior surface 155 of skirt 42 by appropriate means as previously described. As shown in FIG. 7, coupling member 152 includes interior surface features 156 formed complementary to external surface features 158 of skirt 42 to rotationally fix coupling member 152 with skirt 42.

Extending member 154 provides a portion of sensed element 150 which is proximal of exposed exterior surface 155 of skirt 42, and of actuator 50. Referring to the embodiment of FIG. 7, extending member 154 is received between inner wall 90 and outer wall 91 and includes first gear teeth 160 located proximal of dose button 56 and directed radially inward.

Rotation sensor 161 includes a driven internal gear 162 rotatably mounted on post 164 secured to compartment 78. Driven gear 162 includes second gear teeth 166 extending radially outward and intermeshed with first gear teeth 160. Rotation of sensed element 150 causes first gear teeth 160 to rotate second gear teeth 166, and therefore driven gear 162 in rotation about axis 168. Driven gear 162 also includes apertures 170 radially spaced about axis 168.

Rotation sensor 161 further includes an LED 172 attached to compartment 78 proximally of driven gear 162 and positioned in axial alignment with apertures 170 as driven gear 162 rotates about axis 168. An optical receiver 174 is attached to compartment 78 distally of driven gear 162 and is positioned in axial alignment with LED 172 to receive light emitted by LED 172 through apertures 170. Rotation sensor 161 receives light at optical receiver 174 which is periodically interrupted as driven gear 162 rotates, and thereby detects the rotation of sensed element 150 during dose delivery. Rotation sensor 161 provides signals to a controller which determines the amount of dose delivered.

In one aspect, the dose detection system is provided in a modular form. The use of a removably attached module is particularly adapted to use with a medication delivery device in which the actuator and/or the dose setting member include portions external to the medication delivery device housing. These external portions allow for direct attachment of the module containing the rotation sensor to the actuator, such as a dose button, and/or attachment of the sensed element to a dose setting member, such as a skirt, flange, or dose dial member, as described herein. Illustratively, both the module and the sensed element are removably attached to the medication delivery device. Alternatively, the sensed element is provided integral with the medication delivery device and the module is removably attached. The latter approach has the advantage that the more complex and expensive electronics, including the rotation sensor and controller, may be reused with different medication deliver devices. The sensed element may be integral with the medication delivery device as it typically may use relatively simpler, less expensive features. Alternatively, the dose detection system may be provided integrally formed within the medication delivery device and thus is not removed from the device. For example, what is shown and described as the module body 88, instead forms the actuator body of the integrated medication delivery device. Further, what is shown and described as the dose button 56, instead forms an internal body component of the actuator body of the integrated medication delivery device. Further, what is shown and described as the sensed component 100 attached to the skirt 42, instead the sensed component 100 is attached to the flange 38 or dial member 32 of the dose setting member of the integrated medication delivery device. Any of the devices described herein may comprise any one of medications described herein, such as, for example, within cartridge of the device.

The invention claimed is:

1. A medication delivery device comprising:
a device body;
a dose setting member attached to said device body and rotatable relative to said device body about a first axis of rotation during dose delivery;
a sensed element rotationally fixed with said dose setting member, said sensed element including first gear teeth radially-spaced about the first axis of rotation of said dose setting member, said sensed element and said dose setting member being rotatable relative to said device body during dose delivery in relation to an amount of dose delivered;
a rotation sensor attached to the device body proximal to the sensed element and is non-rotatable relative to the device body during dose delivery, said rotation sensor including second gear teeth radially-spaced and rotatable about a second axis of rotation, the second gear teeth being operatively received by the first gear teeth of said sensed element such that the second gear teeth are driven in rotation about the second axis of rotation as the first gear teeth rotate about the first axis of rotation during rotation of said sensed element relative to said device body during dose delivery, said rotation sensor being responsive to the rotation of the second gear teeth to detect the rotation of the dose setting member; and
a controller responsive to said rotation sensor to determine the amount of rotation based on the detected rotation of said dose setting member relative to said device body during dose delivery.

2. The medication delivery device of claim 1 in which the first gear teeth extend radially outward.

3. The medication delivery device of claim 1 in which said rotation sensor comprises an optical, optoelectronic, or magnetic sensor.

4. The medication delivery device of claim 3 in which said rotation sensor comprises an encoder including a drive gear comprising the second gear teeth, in which the encoder includes a body positioned proximally of the first gear teeth, and in which the drive gear is axially-aligned with the first gear teeth.

5. The medication delivery device of claim 1 further comprising an actuator attached to said device body, said actuator being rotationally fixed with said dose setting member and rotatable about the first axis of rotation in a first operating mode during dose setting, the actuator defining an internal compartment, in which said dose setting member extends proximally within the internal compartment of said actuator, in which the rotation sensor is disposed within the internal compartment, and the first gear teeth of said sensed element and the second gear teeth of said rotation sensor are operatively engaged within the internal compartment.

6. The medication delivery device of claim 1 in which the first gear teeth extend radially inward.

7. The medication delivery device of claim 6 in which the second gear teeth extend radially outward.

8. The medication delivery device of claim 5 in which said actuator comprises a dose button and a module attached to said dose button, said module defining the internal compartment comprising said rotation sensor.

9. The medication delivery device of claim 8 in which said dose setting member comprises an exterior surface exposed outside of said device body, said sensed element being attached to the exposed exterior surface.

10. The medication delivery device of claim 9 in which said sensed element is removably attached to the exposed exterior surface.

11. The medication delivery device of claim 9 in which the second gear teeth are axially-aligned with the first gear teeth and with the exposed exterior surface, and in which the module includes an outer wall extending distally to axially cover the first and second gear teeth.

12. A medication delivery device comprising:
a device body;
a dose setting member attached to said device body and rotatable relative to said device body about a first axis of rotation during dose delivery;
a sensed element rotationally fixed with said dose setting member, said sensed element including first gear teeth radially-spaced about the first axis of rotation of said dose setting member, said sensed element and said dose setting member being rotatable relative to said device body during dose delivery in relation to an amount of dose delivered;
a rotation sensor attached to the device body proximal to the sensed element and is non-rotatable relative to the device body during dose delivery, said rotation sensor including second gear teeth radially-spaced and rotatable about a second axis of rotation, the second gear teeth being operatively received by the first gear teeth of said sensed element such that the second gear teeth are driven in rotation about the second axis of rotation as the first gear teeth rotate about the first axis of rotation during rotation of said sensed element relative to said device body during dose delivery, said rotation sensor being responsive to the rotation of the second gear teeth to detect the rotation of the dose setting member; and
a controller responsive to said rotation sensor to determine the amount of rotation based on the detected rotation of said dose setting member relative to said device body during dose delivery, in which said rotation sensor comprises a multi-turn potentiometer.

13. The medication delivery device of claim 1 in which said rotation sensor comprises an encoder including a drive gear comprising the second gear teeth, in which the encoder is attached to the outer wall of said module.

14. The medication delivery device of claim 1, comprising a reservoir of a medication disposed within the device body.

15. A medication delivery device comprising:

a device body;

a dose setting member attached to said device body and rotatable relative to said device body about a first axis of rotation during dose delivery;

a sensed element rotationally fixed with said dose setting member, said sensed element including first gear teeth radially-spaced about the first axis of rotation of said dose setting member, said sensed element and said dose setting member being rotatable relative to said device body during dose delivery in relation to an amount of dose delivered;

a rotation sensor attached to the device body proximal to the sensed element and is non-rotatable relative to the device body during dose delivery, said rotation sensor including a shaft distally extended about a second axis of rotation, second gear teeth attached to the shaft and radially-spaced and rotatable about the second axis of rotation, the second gear teeth being operatively received by the first gear teeth of said sensed element such that the second gear teeth are driven in rotation about the second axis of rotation as the first gear teeth rotate about the first axis of rotation during rotation of said sensed element relative to said device body during dose delivery, said rotation sensor being responsive to the rotation of the second gear teeth to detect the rotation of the dose setting member; and a controller responsive to said rotation sensor to determine the amount of rotation based on the detected rotation of said dose setting member relative to said device body during dose delivery.

16. The medication delivery device of claim 15 in which the first gear teeth extend radially outward, and the second gear teeth extend radially outward.

17. The medication delivery device of claim 15 in which each of said sensed element and said rotation sensor is permanently attached to the device body.

18. The medication delivery device of claim 17 in which said rotation sensor comprises a multi-turn potentiometer.

19. The medication delivery device of claim 18 in which said sensed element is rotationally fixed to said rotation sensor another during dose setting.

20. The medication delivery device of claim 15, comprising a reservoir of a medication disposed within the device body.

* * * * *